United States Patent [19]

Amingual et al.

[11] Patent Number: 4,675,525

[45] Date of Patent: Jun. 23, 1987

[54] MATRIX DEVICE FOR THE DETECTION OF LIGHT RADIATION WITH INDIVIDUAL COLD SCREENS INTEGRATED INTO A SUBSTRATE AND ITS PRODUCTION PROCESS

[75] Inventors: Daniel Amingual; Pierre Felix, both of Grenoble, France

[73] Assignee: Commissariat a l'Energie Atomique, Paris, France

[21] Appl. No.: 820,329

[22] Filed: Jan. 21, 1986

[30] Foreign Application Priority Data

Feb. 6, 1985 [FR] France .............................. 85 01649

[51] Int. Cl.⁴ ...................... G01J 1/00; B44C 1/22; C03C 15/00; B05D 5/06
[52] U.S. Cl. .................................. 250/338; 29/572; 156/643; 156/644; 156/652; 156/655; 156/667; 250/353; 250/515.1; 427/164; 427/264; 427/271; 428/138; 428/142; 430/5; 430/321
[58] Field of Search .................. 430/5, 313, 321, 323; 156/643, 644, 652, 655, 656, 659.1, 661.1, 667, 668; 252/79.4; 204/192 EC, 192 E; 427/164, 264, 271; 357/30, 31, 32; 148/175, 187; 250/338, 353, 515.1; 428/131, 137, 138, 142, 163, 164, 167; 29/572

[56] References Cited

U.S. PATENT DOCUMENTS

| | | | |
|---|---|---|---|
| 3,633,031 | 1/1972 | Pesce et al. | 250/83.3 H |
| 3,963,926 | 6/1976 | Borrello | 250/338 |
| 4,276,335 | 6/1981 | Lemmond | 156/663 X |
| 4,448,865 | 5/1984 | Bohlen et al. | 156/643 X |

FOREIGN PATENT DOCUMENTS 0063694 11/1982 European Pat. Off. .
0068456 1/1983 European Pat. Off. .

OTHER PUBLICATIONS

Patents Abstract of Japan, vol. 6, No. 248, 7.12.1982.

Primary Examiner—William A. Powell

[57] ABSTRACT

The invention relates to a matrix device for the detection of light radiation with individual cold screens integrated into a substrate and to its production process. This device comprises detectors arranged in matrix-like manner and defined in a detection material, a substrate which is transparent to the radiation to be detected and on which is epitaxied the detection material and provided in its upper part with blind holes distributed in matrix-like manner, each hole being positioned facing a detector, a layer of anti-reflecting transparent material covering the bottom of the holes and a layer of a material absorbing the radiation covering the upper face of the substrate and the walls of the holes.

The invention more particularly applies to an infrared imaging system.

15 Claims, 12 Drawing Figures

MATRIX DEVICE FOR THE DETECTION OF LIGHT RADIATION WITH INDIVIDUAL COLD SCREENS INTEGRATED INTO A SUBSTRATE AND ITS PRODUCTION PROCESS

BACKGROUND OF THE INVENTION

The present invention relates to a matrix device for the detection of light radiation with individual cold screens integrated into a substrate and to its production process. The invention particularly applies to an infrared imaging system, such as a camera or an infrared sight using an infrared detector matrix having i row detectors and j column detectors, i and j being independently between 1 and 256, the matrix being illuminated by its rear face through a radiation-transparent substrate.

Figure 1:
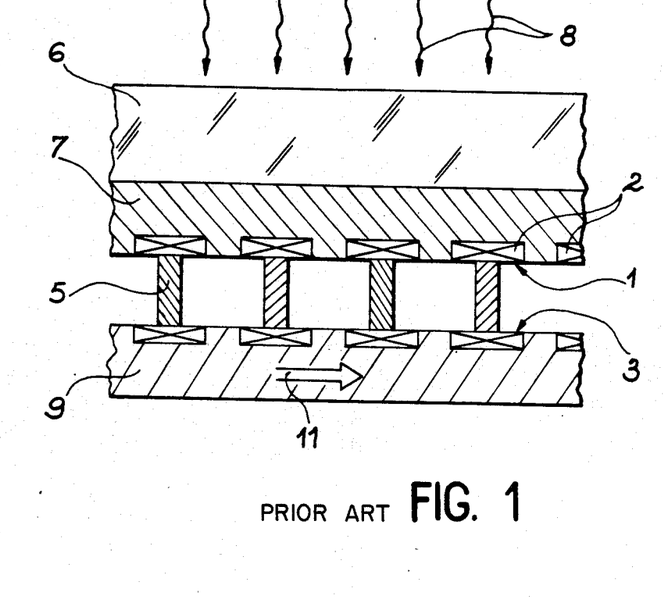
FIG. 1, already described, a prior art infrared imaging device.

FIG. 1 shows a known infrared imaging system constituted in per se known manner by two matrixes, one of which 1 ensures the detection of radiation 8 and the other 3 the reading. These two matrixes 1, 3 are interconnected both mechanically and electrically by metal studs 5. The detectors 2 of detection matrix 1 are e.g. photodiodes made from a semiconductor material 7 by ion implantation or the diffusion of atoms into said material. Semiconductor material 7 is a semiconductor with a small forbidden bandwidth such as $Hg_{1-x}Cd_xTe$, x being between 0 and 1. By adjusting the value of x, it makes it possible to cover a wide wavelength range. This semiconductor material 7 is deposited in thin film form with a thickness of approximately 10 μm by epitaxy on a substrate 6 which is transparent to the radiation 8 to be detected. For radiation 8 in the infrared range, use is made of a material such as cadmium telluride (CdTe), sapphire, gallium arsenide (GaAs) or indium antimonide (InSb).

The reading matrix 3 is made from a semiconductor material 9, such as monocrystalline silicon, by using the procedures currently employed in the production of integrated circuits. The informations relative to each detector 2 are stored, sequentially read and electric signals supplied, which are transmitted by conductors 11 to processing means. In order to reduce the incident photon flux on the detector matrix 1, it is general to associate a single screen with all the matrix 1 of detectors of a screen with each detector 2 of said matrix 1, said screens being cooled in order to limit heat radiation. These screens make it possible to reduce the incident flux in such a way that each detector 2 constituting matrix 1 has a viewing angle which is as close as possible to the numerical aperture of the optics from which the radiation 8 comes. The reduction of the photon flux makes it possible to reduce the background noise of the detectors and improve there efficiency. It also makes it possible to reduce the direct current supplied by each detector 2 and consequently increase the integration time by the reading matrix 3 for a given storable charge quantity of the elements of said reading matrix 3.

Figure 2:
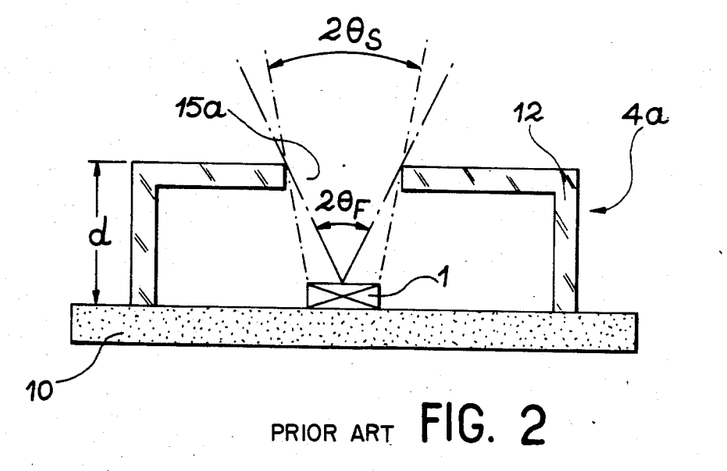
FIG. 2, already described, a matrix of detectors associated with a collective cold screen also of a known type.

FIG. 2 shows a detector matrix 1 associated in known manner with a single cold screen. The latter is generally constituted by a ceramic 10 cooled by a liquefied gas and in the centre of which is placed the detector matrix 1, whilst around said ceramic are positioned the walls 12 of screen 4a cooled by heat contact with said ceramic 10.

The cold screen 4a with an opening 15a facing the detector matrix 1 is placed at a distance d above the same. The numerical aperture of the optics from which the radiation comes is represented by the angle $2\theta_S$, whilst the angle $2\theta_F$ represents the angle under which the centre of the detector matrix 1 sees the incident radiation.

The efficiency of the cold screen is defined as the ratio between the effective solid angles $\Omega_S = n\sin^2\theta_S$ corresponding to the angle $\theta_S$ and $\Omega_F = n\sin^2\theta_F$ corresponding to the angle $\theta_F$. Thus, the cold screen efficiency n is equal to:

$$\eta = \frac{\sin^2\theta_S}{\sin^2\theta_F}$$

n consequently representing the ratio between the incident light radiation reaching the aperture of the cold screen and the light radiation detected by the detection matrix.

With such a device, the larger the size of the detector matrix 1 and the smaller the aperture 15a of the cold screen 4a, the more difficult it is to obtain a good efficiency n. Moreover, the radiation detected is not uniform over the entire matrix 1 of detectors, being smaller at the edges than in the centre of the matrix.

In order to obviate these disadvantages, consideration has been given to the association of an individual cold screen with each of the detectors of a detection matrix 1. These individual cold screens appear as a system of holes made in a material and given the same spacing as the detectors.

Such individual cold screens are more particularly described in U.S. Pat. No. 3,963,926 of Jan. 9, 1975, and U.S. Pat. No. 4,446,372 of Jul. 1, 1981. Compared with the collective cold screen, individual cold screens have advantages such as the possibility of increasing the dimensions of the matrix without changing the geometry of the holes and consequently retaining the same efficiency, a homogeneous illumination over the entire detection matrix, there being no attenuation on the matrix edges and an increase in the cooling speed and consumption.

U.S. Pat. No. 3,963,926 describes a process for the production of individual cold screens associated with detectors defined in a slice of an absorbing material, such as p+ doped silicon. This silicon is etched over its entire thickness by an etching solution following the preferred locations defined by masks. The thus perforated silicon is fixed to a substrate by an epoxy resin. The upper face of the substrate supports a matrix of detectors, each hole facing one matrix detector.

This production process suffers from certain disadvantages. In particular the thus formed cold screens constitute a part fitted to the detection system. Moreover, if the material forming these screens is too thick, the walls of the openings stop part of the radiation and the efficiency of such cold screens is mediocre. Moreover, the closely spaced openings formed in the silicon weaken the structure of such cold screens.

U.S. Pat. No. 4,446,372 describes a process for the production of individual cold screens associated with detectors defined in a substrate transparent to the light radiation to be detected. These detectors are e.g. formed by ion implantation in a conduction material epitaxied on the transparent substrate. A thin opaque film of an absorbing or reflecting material with openings is deposited on the upper face of the substrate. Thus, the detectors are positioned facing the optics from which the light radiation through the substrate comes and the openings of the opaque deposit. This opaque film protects the detectors from electromagnetic radiation and improves detection. This detection has a very limited application due to the large aperture of the viewing angle of these detectors. Thus, an extreme ray of a beam reaching an opening can reach a detector close to that facing the opening.

SUMMARY OF THE INVENTION

The present invention relates to a matrix device for the detection of light radiation having a matrix of detectors associated with individual cold screens and to its production process, which makes it possible to obviate the disadvantages of the different detection devices described hereinbefore. By using a number of simple operations, this process makes it possible to obtain a rigid detection device, without fitted parts, which has a good cold screen efficiency.

More specifically the invention relates to a matrix detection device for light radiation comprising detectors, distributed in matrix-like manner and defined in a detection material, and individual cold screens, wherein it comprises a radiation transparent substrate on which is epitaxied the detection material and provided in its upper part with blind holes arranged in matrix-like manner, each hole facing a detector, an anti-reflecting transparent material layer covering the bottom of the holes and making it possible to improve the photoresponse of the detectors and a layer of a material absorbing the radiation covering the upper face of the substrate and the walls of the holes making it possible to improve the cold screen efficiency.

Advantageously a layer of a material opaque to the radiation covers at least part of the periphery of the bottom of the holes, so as to define accurately the detection sensitive surface. This radiation-opaque material is preferably a radiation-absorbing material.

The transparent anti-reflecting material makes it possible to transmit the radiation reaching the same. However, the absorbent material absorbs the radiation striking it. For a given detector, the association of these two materials makes it possible to eliminate the stray radiation, e.g. from the reflected rays or rays not coming from the corresponding blind hole.

The invention also relates to a process for the production of a matrix device for the detection of light radiation comprising detectors and cold screens distributed in matrix-like manner wherein it comprises the following stages:

(a) epitaxy of a detection material on the lower face of a radiation-transparent substrate, (b) formation of detectors in the detection material layer, (c) formation of a mask on the upper face of the substrate opposite to the lower face, so as to mask those parts of the substrate not facing said detectors, (d) etching the upper part of the substrate through the mask to form blind holes, (e) deposition of a layer of an anti-reflecting transparent material on the upper etched face of the substrate, the walls and the bottoms of the holes, (f) deposition of a layer of a radiation-absorbing material on the anti-reflecting transparent material layer, at least above the upper face of the substrate and the walls of the holes.

According to a preferred embodiment of the inventive process, as the radiation is infrared radiation, the substrate is of cadmium telluride.

According to another preferred embodiment of the process, the infrared radiation detection material is $Hg_{1-x}Cd_xTe$.

According to another preferred embodiment of the inventive process, stage (c) consists of depositing on the upper face of the substrate an etching-resisting protecting layer, forming a resin mask on the protecting layer and etching the protecting layer through the resin mask.

According to a preferred embodiment of the inventive process, the protecting layer is an alumina layer.

According to another embodiment of the inventive process, the protecting layer is a metal layer.

According to another embodiment of the process, stage (d) is performed by ionic machining.

According to another embodiment of the inventive process, as the radiation is infrared radiation, the anti-reflecting transparent material is zinc sulphide. Advantageously, the absorbent material is an absorbent semiconductor or a metal.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 3:
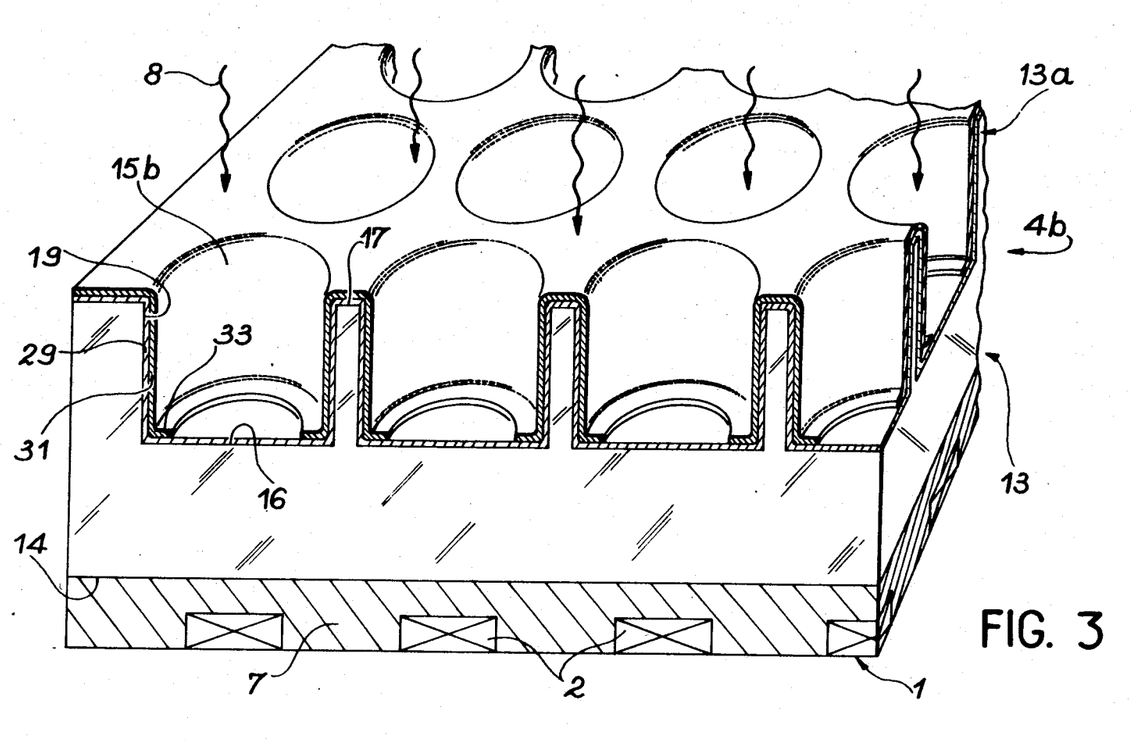
FIG. 3, in perspective a detection device formed from a matrix of detectors associated with individual cold screens according to the invention.

FIG. 3 shows shows a device according to the invention having a matrix 1 of detectors 2 associated with individual cold screen 4b.

The detectors, which are in particular in the form of a rectangular parallelepiped, are implanted in a semiconductor material 7, such as $Hg_{1-x}Cd_xTe$, x being between 0 and 1 with a thickness of about 10 μm. This material 7 is epitaxied on the lower face 14 of a substrate 13 transparent to the light radiation 8 to be detected. Substrate 13 is more particularly made from CdTe with a thickness of about 100 μm. In said substrate 13 is provided a system of blind holes 15b with a depth of about 50 μm and having the same spacing as the detectors 2. In other words, there is a single hole 15b facing each detector 2. In part, these holes 15b constitute the individual cold screens 4b. Holes 15b must have the largest surface compatible with the spacing of detectors 2 to permit a high sensitive surface per detector 2.

The shape of holes 15b is a function of that of detectors 2. In the represented case, it can be circular, square or intermediate. The circular shape favours the effectiveness or efficiency of the cold screen, whilst it reduces the sensitive detection surface. The upper face 17 of transparent substrate 13, the walls 19 and the bottom 16 of holes 15b are covered with a layer 29 of an antireflecting transparent material in order to improve the photo-response of detectors 2. This only constitutes an exemplified embodiment and consideration can be given to only covering the bottom of the holes with an antireflecting transparent material. In order to improve the efficiency of these cold screens, the vertical walls 19 of the holes 15b, as well as the upper face 17 of transparent substrate 13 are covered with a second layer 31 of a substance absorbing the light radiation 8.

Moreover, in order to accurately define the sensitive surface of each detector, which can fluctuate between individual detectors, a layer 33 of a material opaque to light radiation can be provided on the periphery of the bottom 16 of each hole 15b. Layer 33 can be made from an absorbing or reflecting material.

Figure 4:
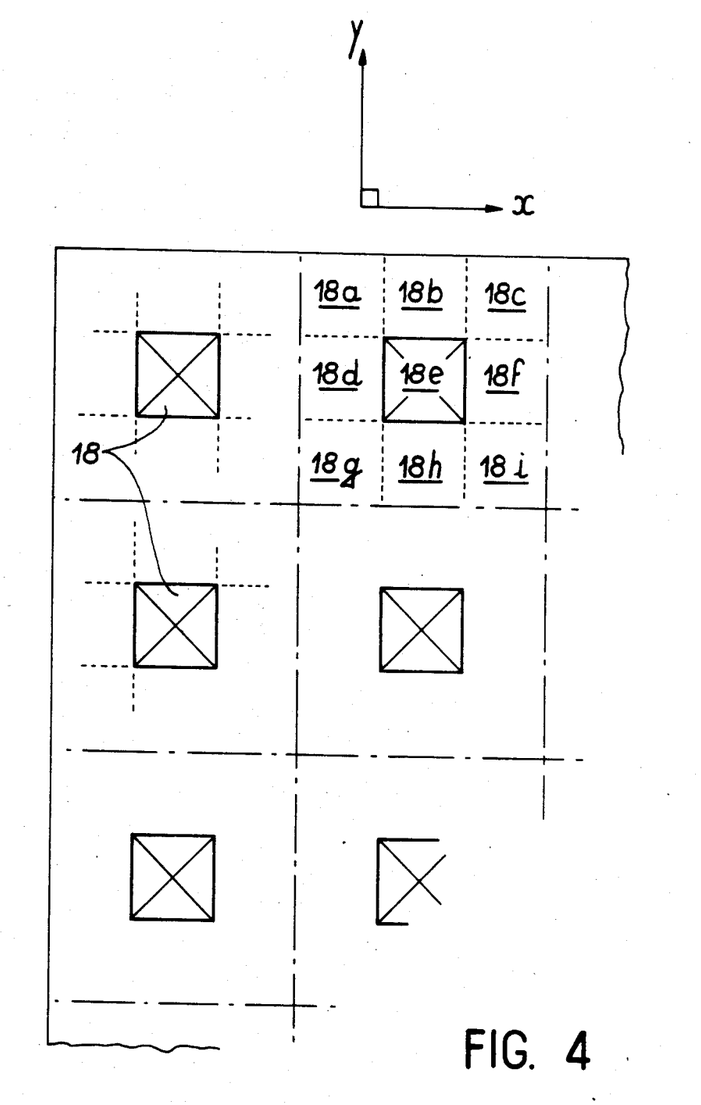
FIG. 4, a matrix of detectors with bidirectional displacement of each detector in accordance with nine elementary positions.

In FIG. 3 the cold screens are associated with fixed detectors 2, but can also be applied to a matrix of much more widely spaced detectors used in known unidirectional or bidirectional optomechanical scanning systems. A matrix of detectors bidirectional scanning is shown in FIG. 4. In such matrixes, each detector 18 is displaced in one or two directions x or y contained in the matrix plane by mechanical action in n or n×n elementary positions, respectively for a unidirectional or bidirectional scan. It successively receives during an image time, the informations relative to n or $n_2$ elementary image points, respectively for a unidirectional or bidirectional scan.

FIG. 4 shows a detector matrix with bidirectional scanning, n being equal to 3. Thus, each detector 18 has nine elementary positions from 18a to 18i. As a result of the larger spacing between the detectors, the holes in a substrate transparent to the light radiation to be detected can be deeper and approximately 100 μm, so that the viewing angle of each detector is more more closed.

Figure 5:
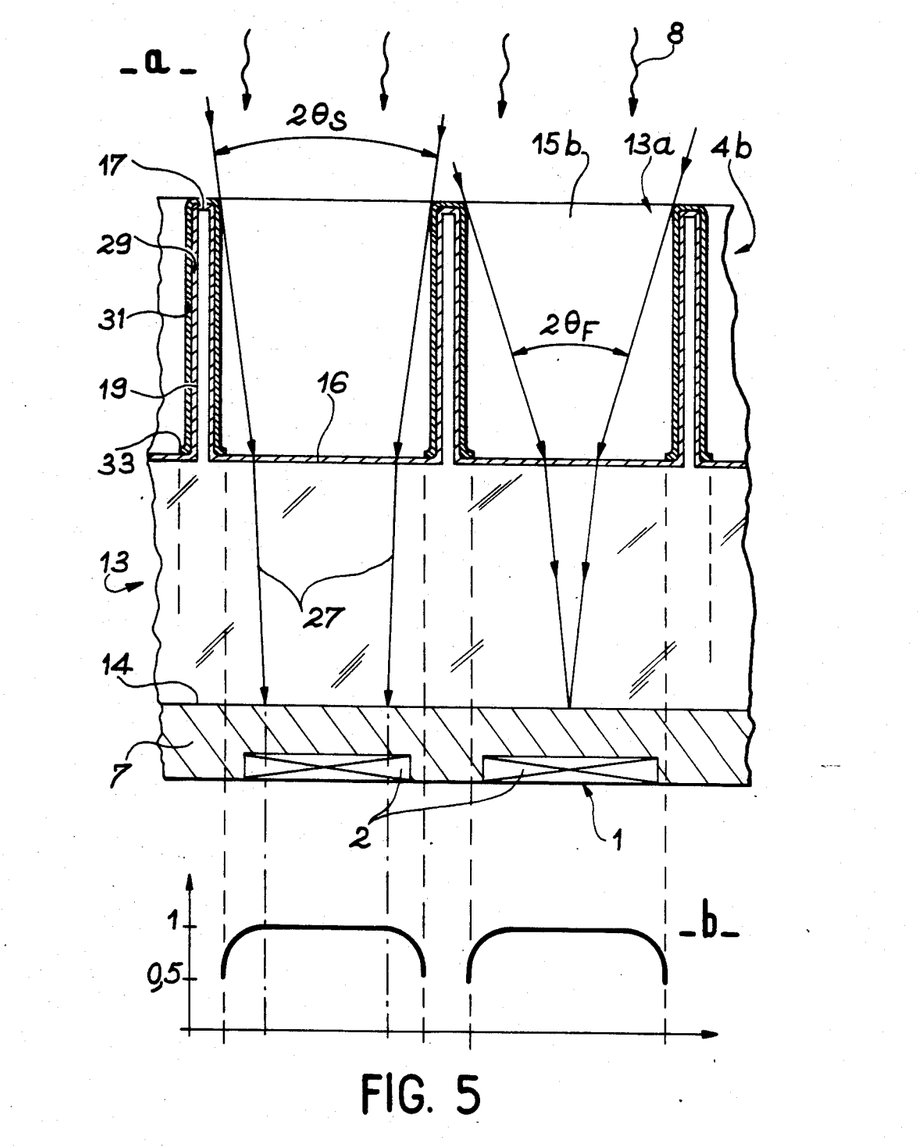
FIG. 5, part a, the illumination of the device of FIG. 3 and part b, the profile of the illumination obtained with such a device.

FIG. 5 diagrammatically shows in part a a longitudinal section of a device according to FIG. 3 of a matrix 1 of detectors 2 associated with individual cold screen 4b and in its part b the profile of the illumination obtained with such a structure.

Part a once again has detectors 2 implanted in a conductive material 7 epitaxied on the lower face 14 of a substrate 13 transparent to the light radiation 8 to be detected. The upper face 17 of substrate 13, the walls 19 and the bottom 16 of holes 15b are covered with a layer 29 of a transparent anti-reflecting material. Except at the bottom 16 of holes 15b, layer 29 is covered with a layer 31 of a material absorbing the radiation 8 to be detected. On the periphery of holes 15b is deposited a layer 33 of a material which is opaque to the radiation. The aperture of the optics from which the radiation comes is represented by the angle $2\theta_S$ whilst angle $2\theta_F$ represents the angle under which the centre of a detector sees the light radiation 8. The extreme light rays 27 transmitted by substrate 13 define the maximum sensitivity zone of a detector 2. With such a structure, it can be seen in part b of FIG. 5 that the illumination from the optics from which radiation 8 comes, standardized to the unit, is maximum on the central surface of each detector, representing approximately half its surface. The illumination then decreases on the edges of the detectors 2 to 50% of its maximum value.

The efficiency n of the individual cold screens 4b is calculated on the basis of the formula:

$$\eta = \frac{\sin^2\theta_S}{\sin^2\theta_F}$$

Thus, with a 100 μm thick CdTe substrate, 50 μm deep holes an aperture of the optics from which the radiation comes corresponding to an angle $\theta_S=10°$, there is a cold screen efficiency of approximately 26% for a thickness between the walls 19 less than 3 μm and 23% for a thickness between walls 19 of 3 μm.

For a matrix of detector spaced in the manner shown in FIG. 4 associated with individual cold screens, as the depth of the holes is greater and the angle $\theta_F$ is more closed, the screens have a greater efficiency n.

FIGS. 6a to 6g represent the different stages of the process of producing a matrix device for the detection of light radiation incorporating matrix detectors associated with individual cold screens.

Figure 6A:
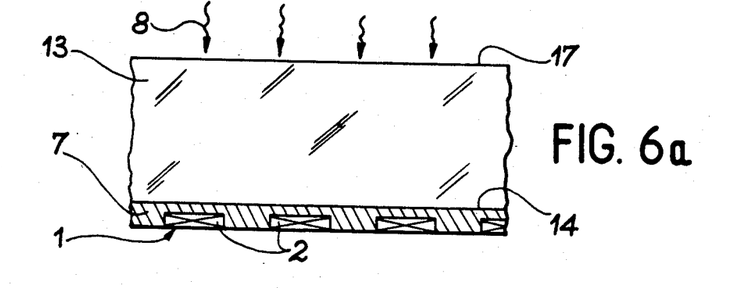
FIGS. 6a to 6g the different stages of the process for the production of the detector matrix with individual cold screens integrated into a transparent substrate.

As shown in FIG. 6a, the first stage of the process consists of defining a matrix 1 of detectors 2 by implanting ions or diffusing atoms into a semiconductor material 7 epitaxied on the lower face 14 of a substrate 13 transparent to the light radiation 8 to be detected and with a desired thickness. This matrix of detectors can be formed either before the production of the individual cold screens, as defined here, or at the end of the production of such screens. In the case of an infrared detection device, the semiconductor material 7 can be $Hg_{1-x}Cd_xTe$, x being between 0 and 1 and with a thickness of 10 μm epitaxied onto a CdTe substrate 13 transparent to infrared radiation. The original CdTe substrate has an average thickness of 500 μm and its thickness is consequently previously reduced by conventional mechanical and chemical means to about 100 μm.

Figure 6B:
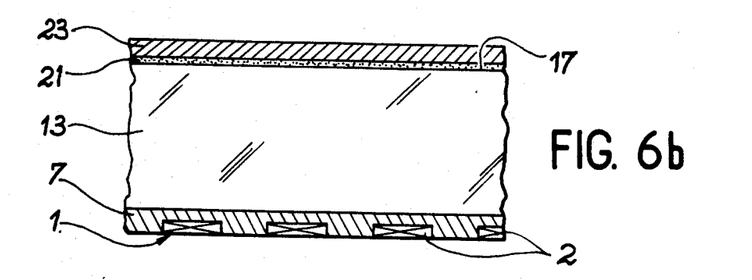

As illustrated in FIG. 6b, the following stage consists of depositing on the upper face 17 of substrate 13 a first protective layer 21 of a material resistant to ionic or reactive ionic etching, as a function of the type of machining used for etching substrate 13. Protective layer 21 can be an alumina layer with a thickness of 2 μm or a layer of a metal such as platinum, nickel or chrome with a thickness of e.g. 1 μm. This protective layer 21 can be deposited by cathodic sputtering.

This is followed by the deposition on protective layer 21 of a second layer 23 of a positive or negative photosensitive resin, e.g. a positive resin such as resin AZ 1350 of thickness 4 μm.

Figure 6C:
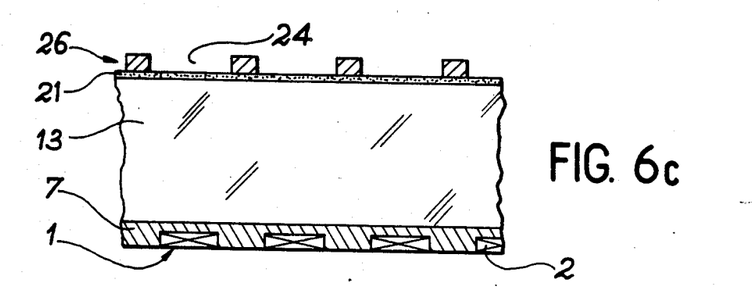
Figure 6D:
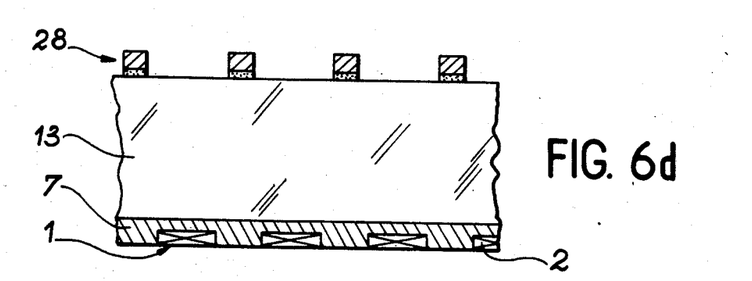

The following stage, as illustrated in FIG. 6c, consists of producing a resin mask 26 having openings 24 facing each detector 2, by local irradiation of the photosensitive resin layer 23 and then the development thereof. The openings 24 to be made are aligned facing each detector 2, e.g by positioning detectors 2 relative to a cross-hair. The detector 2 and substrate 13 are fixed, then turned to align openings 24 to be made in resin 23 with marks made at the end of the cross-hair. It is also possible to align detectors 2 and openings 24 to be formed in a single operation using two facing microscopes having the same optical axis, alignment then taking place by means of video monitors.

The following stage, as illustrated in FIG. 6c consists of etching through mask 26 the entire thickness of protective layer 21 using either chemical etching or ionic machining. For an alumina protective layer, etching can be carried out chemically using a solution of $H_3PO_4$ and isopropyl alcohol at a temperature of 80° C. or a 10% $H_2SO_4$ solution at 40° or 60° C. For a metallic protective layer 21, said etching can be carried out by ionic machining. The thus etched layer 21 and the resin mask 26 constitute a two-coating mask 28 for etching substrate 13.

Figure 6E:
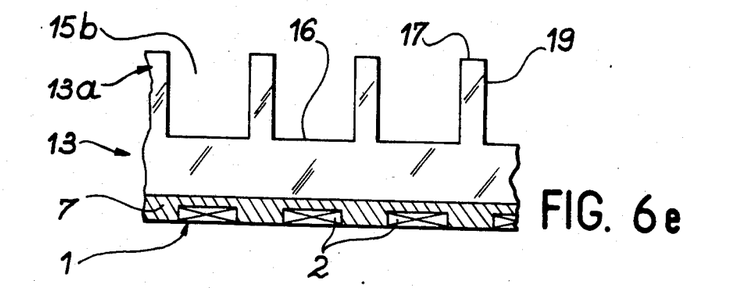

The following stage illustrated in FIG. 6e consists of etching blind holes 15b in the upper part 13a of transparent substrate 13 by ionic or reactive ionic machining, at the locations not masked by the etched resin layer 23 and protective layer 21, the latter then disappear during the etching of holes 15b. With the following etching speeds : alumina 100 Å/mn, resin AZ 1350 300 Å/mn and CdTe 1500 Å/mn, the 4 μm thick resin layer 21 added to the 2 μm thick alumina layer 23 require the same etching time as the 50 μm thick CdTe substrate 13. When protective layer 21 is a metal layer, substrate 13 is etched under a partial oxygen pressure to slow down the etching speed of the metal which exceeds 500 Å/mn to less than 50 Å/mn.

Figure 6F:
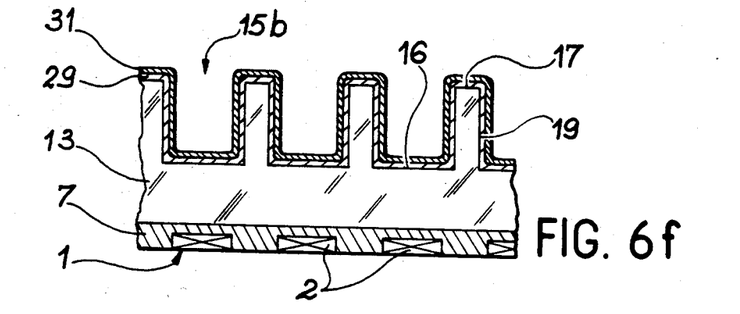

The following stage illustrated in FIG. 6f consists of depositing on the entire surface indented by the holes 15b of substrate 13, i.e. on the upper face 17 of substrate 13, on the walls 19 and the bottom 16 of holes 15b, a first layer 29 of an anti-reflecting transparent material, followed by a second film 31 of a material absorbing the light radiation 8 to be detected. The anti-reflecting transparent material is e.g. constituted by approximately 1 μm thick zinc sulphide for infrared radiation with a wavelength between 8 and 12 μm, whilst the thickness is 0.5 μm for infrared radiation with a wavelength between 3 and 5 μm. The layer 31 of a material absorbing infrared radiation is deposited in thin film form, of less than 1 μm, on the anti-reflecting transparent material layer 29 by the evaporation of an absorbent semiconductor or a metal such as gold, under a residual oxygen pressure or chemically.

Figure 6G:
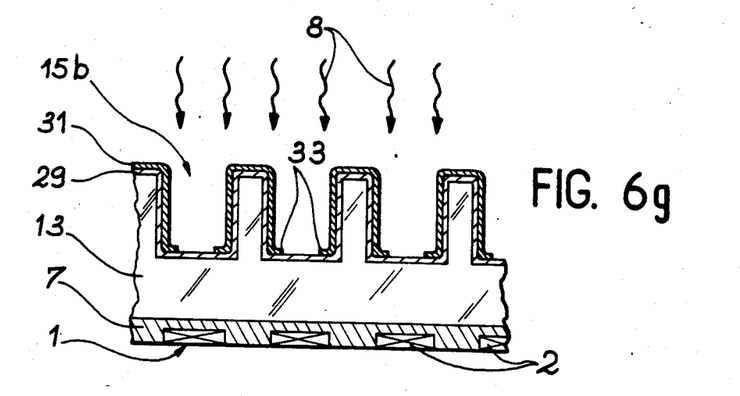

The final stage of the production process shown in FIG. 6g consists of etching the absorbent layer 31, so as to eliminate the absorbent material from the entire surface or from the central surface of the bottom of holes 15b to obtain the desired sensitive detecting surface. Etching of the bottom of the holes 15b of absorbent layer 31 takes place e.g. by ionic etching methods carried out through a resin mask. This can be obtained by the deposition of a resin, irradiation and development of said resin. The deposition of the resin e.g. takes place with the aid of a machine involving deposition by a mist of electrostatically charged particles. The irradiation of the resin at the bottom of the holes 15b can be carried out with a machine by projection, which gives a much greater accuracy in use than a conventional contact positioner.

The absorbent layer 31 can be directly deposited on the upper face of substrate 17 and the walls 19 of holes 15b by the evaporation of absorbent material on substrate 13. The latter is then placed on a rotary support, inclined in such a way that the particles of the absorbent material are deposited down to the bottom of walls 19 of holes 15b.

When there is no absorbent material at the bottom of holes 15b, it is possible to deposit a layer 33 of a radiation-opaque material, such as a reflecting or absorbing material, on the periphery of the bottom of the holes 15b to define the sensitive detection surface.

In the detection device according to the invention, the individual cold screens are integrated into the substrate, whilst not being formed by a fitted together part as in the prior art. Moreover, the different stages of forming these screens use known etching and deposition procedures, which can be easily realised.

What is claimed is:

1. A matrix device for the detection of light radiation provided with a matrix of detectors defined in a detection material and with individual cold screens, comprising a radiation-transparent substrate, on which is epitaxied the detection material and provided in its upper part with a matrix of blind holes, each hole facing a detector, a layer of transparent anti-reflecting material covering the bottom of the holes and a layer of a radiation-absorbing material covering the upper face of the substrate and the walls of the holes.

2. A device according to claim 1, wherein a layer of an opaque material at least partly covering the periphery of the bottom of the holes is provided.

3. A process for the production of a matrix device for the detection of light radiation provided with a matrix of detectors and of cold screens, comprising the following stages:
    (a) epitaxy of a detection material on the lower face of a radiation-transparent substrate,
    (b) formation of detectors in the detection material layer,
    (c) formation of a mask on the upper face of the substrate opposite to the lower face, so as to mask those parts of the substrate not facing said detectors,
    (d) etching the upper part of the substrate through the mask to form blind holes,
    (e) deposition of a layer of an anti-reflecting transparent material on the upper etched face of the substrate, the walls and the bottoms of the holes,
    (f) deposition of a layer of a radiation-absorbing material on the anti-reflecting transparent material layer, at least above the upper face of the substrate and the walls of the holes.

4. A process according to claim 3, wherein as the radiation is infrared radiation, the substrate is of cadmium telluride.

5. A process according to claim 3, wherein the infrared radiation detection material is of $Hg_{1-x}Cd_xTe$.

6. A process according to claim 3, wherein stage c consists of depositing on the upper face of the substrate a protective layer, forming a resin mask on the protective layer and etching said layer through the mask.

7. A process according to claim 6, wherein the protective layer is an alumina layer.

8. A process according to claim 7, wherein the etching of the alumina layer takes place with an etching solution containing orthophosphoric acid and isopropyl alcohol at 80° C.

9. A process according to claim 7 wherein the etching of the alumina layer takes place with a 0.1 m sulphuric acid solution at a temperature between 40° and 60° C.

10. A process according to claim 6, wherein the protective layer is a metal layer.

11. A process according to claim 10, wherein the etching of the metal layer takes place by ionic machining.

12. A process according to claim 3, wherein stage d is performed by ionic machining.

13. A process according to claim 3, wherein as the radiation is infrared radiation, the transparent anti-reflecting material is zinc sulphide.

14. A process according to claim 3, wherein the absorbent material is an absorbent semiconductor.

15. A process according to claim 3, wherein the absorbent material is a metal.

* * * * *